United States Patent [19]

Rosenthal

[11] Patent Number: 5,077,476

[45] Date of Patent: Dec. 31, 1991

[54] INSTRUMENT FOR NON-INVASIVE MEASUREMENT OF BLOOD GLUCOSE

[75] Inventor: Robert D. Rosenthal, Gaithersburg, Md.

[73] Assignee: Futrex, Inc., Gaithersburg, Md.

[21] Appl. No.: 565,302

[22] Filed: Aug. 10, 1990

Related U.S. Application Data

[63] Continuation-in-part of Ser. No. 544,580, Jun. 27, 1990.

[51] Int. Cl.⁵ ............................................. G01N 21/35
[52] U.S. Cl. .................................. 250/341; 250/339; 250/343
[58] Field of Search ....................... 250/339, 341, 343; 356/39; 128/633

[56] References Cited

U.S. PATENT DOCUMENTS

| 4,655,255 | 4/1987 | Döhne et al. | 128/633 |
| 4,882,492 | 11/1989 | Schlager | 250/341 |
| 4,883,953 | 11/1989 | Koachi et al. | 250/341 |

Primary Examiner—Jack I. Berman
Assistant Examiner—Richard Hanig
Attorney, Agent, or Firm—Rothwell, Figg, Ernst & Kurz

[57] ABSTRACT

Near-infrared quantitative analysis instruments non-invasively measure blood glucose by analyzing near-infrared energy following interactance with venous or arterial blood, or transmission through a blood containing body part. A replaceable cartridge stores data unique to an individual patient/user. The analysis instruments are accurate and readily lend themselves to at-home testing by diabetics.

27 Claims, 8 Drawing Sheets

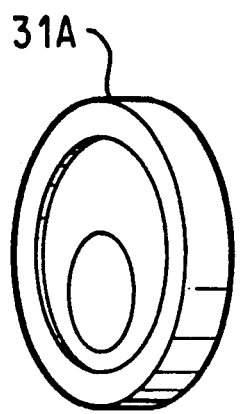
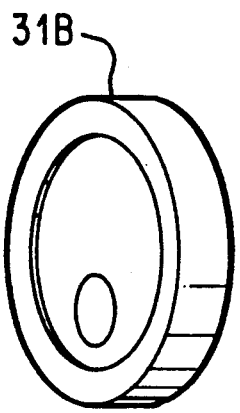
FIG. 8A     FIG. 8B
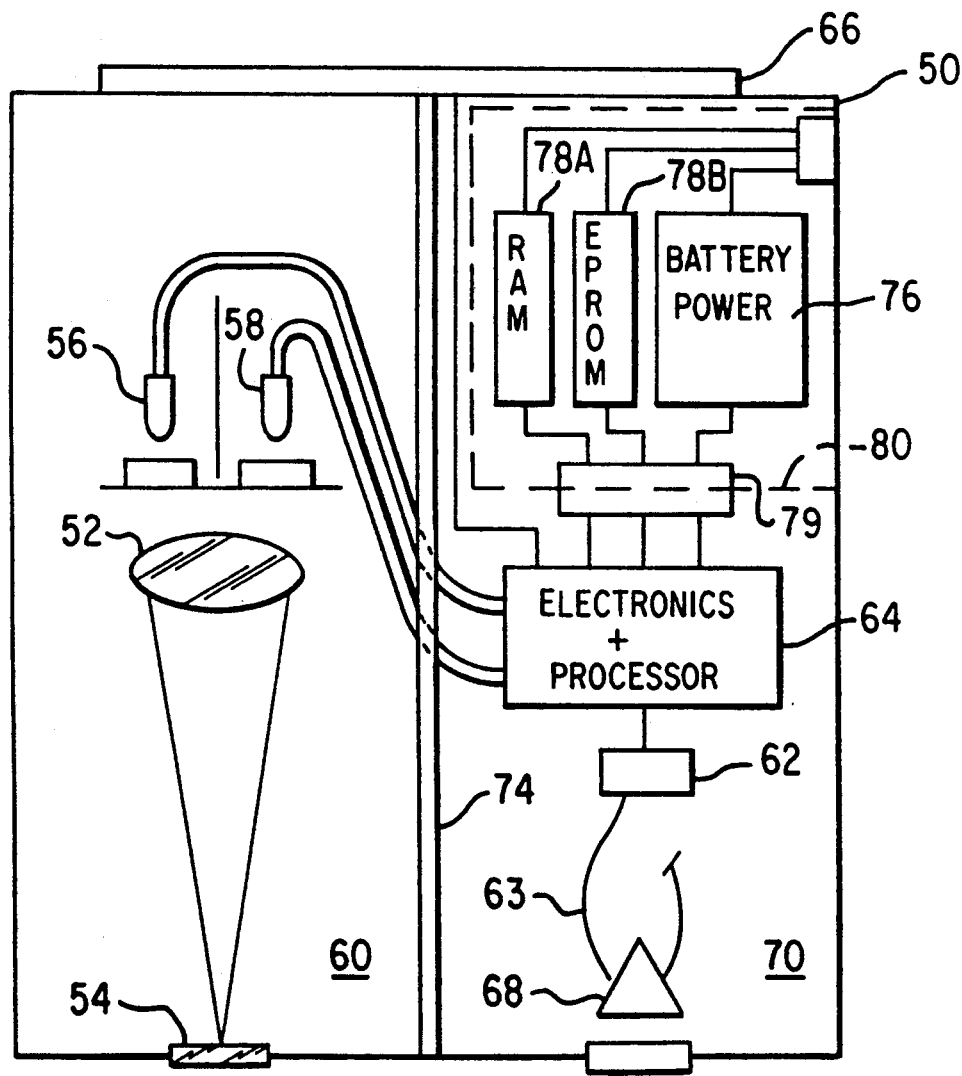
FIG. 9

INSTRUMENT FOR NON-INVASIVE MEASUREMENT OF BLOOD GLUCOSE

CROSS-REFERENCE TO RELATED APPLICATION

This application is a continuation-in-part of copending application Ser. No. 07/544,580, filed on June 27, 1990.

BACKGROUND OF THE INVENTION

1. Field of the Invention

This invention relates to instruments and methods for the non-invasive quantitative measurement of blood glucose. More particularly, this invention provides a hand-held blood glucose analysis instrument including a replaceable cartridge containing data concerning a particular patient.

2. Description of Background Art

Information concerning the chemical composition of blood is widely used to assess the health characteristics of both people and animals. For example, analysis of the glucose content of blood provides an indication of the current status of metabolism. Blood analysis, by the detection of above or below normal levels of various substances, also provides a direct indication of the presence of certain types of diseases and dysfunctions.

One method of determining blood chemistry is by removing a sample of blood (e.g. 5–10 ml) and performing one or more standard chemical tests. These types of tests are moderately expensive, and often require one class of trained technicians to remove the blood and another class of trained technicians to perform the chemical tests. Moreover, the results of the blood tests often are not available for several hours, and sometimes even several days.

An alternative type of technology, namely self-contained instruments, has been introduced for relatively rapid blood screening of a large number of subjects. These instruments, in general, use a much smaller blood sample (approximately 0.25 ml) from a "finger poke." This small blood sample is placed on a chemically-treated carrier and entered into the instrument. These instruments normally provide either an individual analysis (e.g. glucose level) or multiple analyses in a few moments. These types of instruments unfortunately are quite costly, e.g., in the range of several thousand dollars.

A third class of blood instrumentation is available for the specific purpose of determining glucose level in people with diabetes. This technology also uses a small sample from a finger poke and the sample is placed on a chemically treated carrier which is inserted into a portable battery operated instrument. In general, these instruments provide a single function; i.e. measurement of glucose. Although these specialized instruments are relatively low cost, the cost of the disposable carrier "stick" must be considered. Since some diabetic patients may require glucose analysis four or more times a day, the cost over a period of a year can become significant.

Current glucose analytical systems require blood to be extracted from the body prior to performing the analysis. This blood withdrawal requirement limits the application of such testing; many people who may be interested in knowing their glucose level are reluctant to have either their finger poked or blood samples removed by hypodermic needle. This reluctance or anxiety in allowing blood sample removal is due to concern over the possibility of infection, discomfort (pain) and generalized patient fear.

Thus, there is a great need for non-invasive analytical instruments and methods that would provide essentially the same accuracy as conventional blood glucose tests. Moreover, there is a need for a non-invasive low-cost method for measurement of glucose in diabetic patients. In particular, there is a need for a low-cost hand-held non-invasive blood glucose analysis instrument.

Near-infrared (sometimes referred to herein as simply "near-IR") quantitative analysis is widely used in the field of agriculture for determining chemical compositions within grain, oilseeds, and other agricultural products. As an example, near-IR energy reflected from the surface of finely ground seeds and grain provides information concerning protein and moisture content. For a general introduction to near infrared quantitative analysis, see "An Introduction to Near-Infrared Quantitative Analysis" presented by Robert D. Rosenthal at the 1977 Annual Meeting of American Association of Cereal Chemists. Near-infrared technology has been extended to allow totally non-destructive measurements by using light transmission through a sample as discussed in "Characteristics of Non-Destructive Near-Infrared Instruments for Grain and Food Products" by Robert D. Rosenthal, presented at the 1986 Meeting at the Japan Food Science Institute. Although this transmission approach avoids the need to finely grind the sample, it is not suited for use where access to two opposite surfaces is not available.

One example of this transmission approach is provided in U.S. Pat. No. 4,621,643 (New, Jr. et al., 1986) which relates to an optical oximeter apparatus for determining pulse rate and degree of arterial oxygen saturation. Light energy is passed through an appendage of the body, e.g. a finger, and strikes a detector positioned on a side of the appendage opposite from the light source. Pulse rate and saturated oxygen are calculated from coefficients of extinction of light at the selected wavelengths.

SUMMARY OF THE INVENTION

In accordance with the present invention, a near-infrared quantitative analysis instrument for measuring blood glucose comprises means for introducing near-IR energy into blood present in a body part of a subject, means for detecting near-IR energy emerging from the subject, means for converting an electrical signal corresponding to the detected energy into a readout indicative of the quantity of glucose present in the blood of the subject, and means for positioning the introducing means and detecting means adjacent to the body part of the subject.

In accordance with another aspect of the invention, a near-infrared quantitative analysis instrument comprises means for measuring blood glucose via near-IR transmission through a blood-containing body part, the instrument including means for introducing near-IR energy into one side of a body part, means for detecting near-IR energy emerging from an opposite side of the body part and means for positioning the near-IR introducing and detecting means on opposite sides of the body part.

The analysis instrument is comprised of a lightweight, hand-held instrument including a base housing unit and a replaceable cartridge means which engages the base unit. The replaceable cartridge includes a memory device for storing data associated with a particular patient and the particular base unit, and may also include the power source for the analysis instrument. The data stored in the replaceable cartridge may include a series of glucose readings and calibration constants custom calibrated for the individual user.

BRIEF DESCRIPTION OF THE DRAWINGS

FIGS. 8A nd 8B show different sized finger inserts for the glucose measurement instrument;

FIG. 9 shows an interactance type non-invasive glucose measurement instrument according to one embodiment of the present invention.

DETAILED DESCRIPTION OF THE PREFERRED EMBODIMENTS

According to one embodiment of the invention utilizing near-IR transmission analysis techniques, near-IR light energy at bandwidths centering on one or more wavelengths of interest is transmitted through a blood-containing portion of the body of a test subject. The near-IR energy emerges from the test subject, generally opposite from the near-IR source, and is detected by a detector. Following amplification of the detector-generated signal, the amplified output is processed into an output signal indicating the amount of glucose in the subject's blood.

Figure 1:
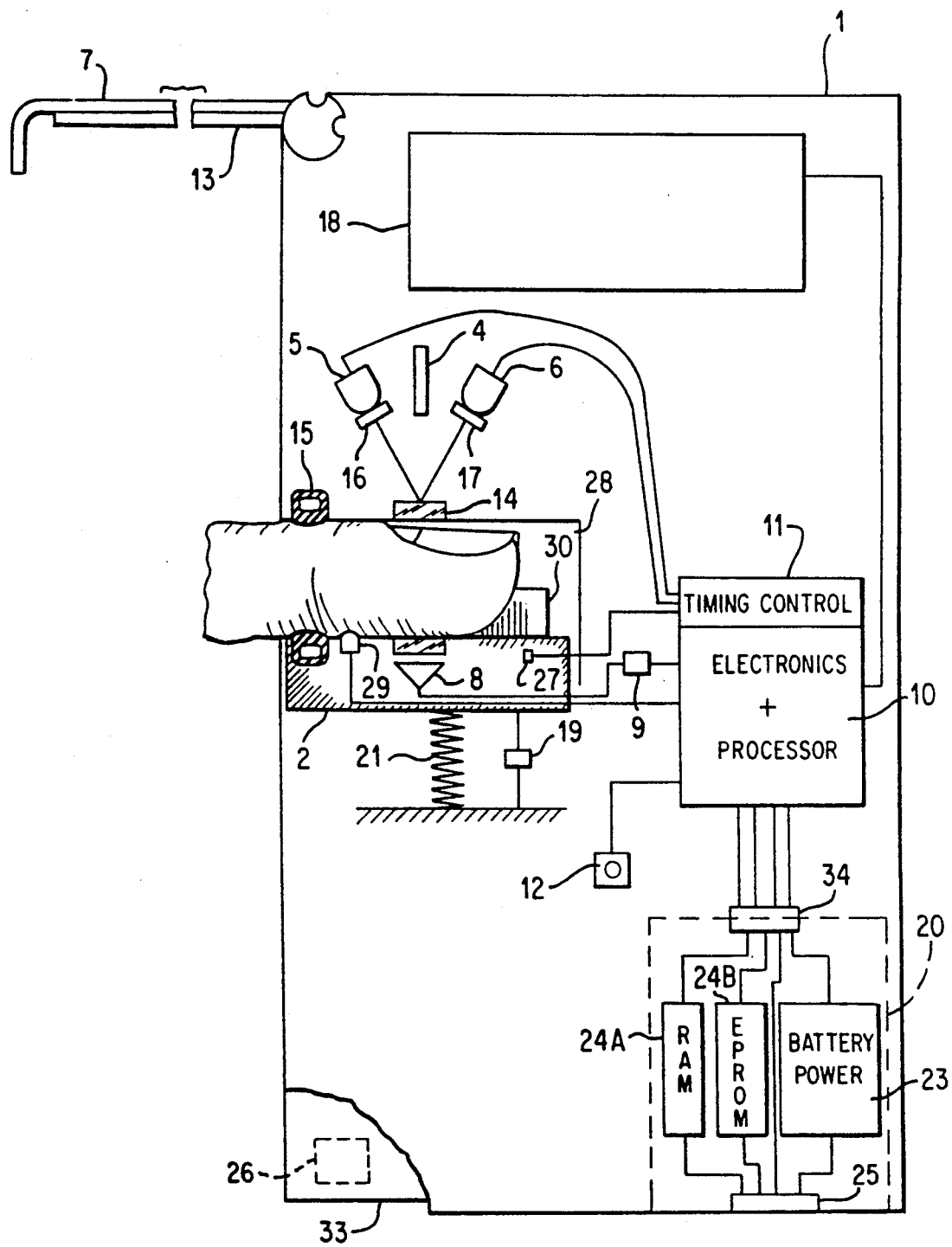
FIG. 1 illustrates a non-invasive glucose measurement instrument according to one embodiment of the present invention.

FIG. 1 illustrates a non-invasive Self Monitoring Glucose Meter (NISMGM) 1 which is designed to measure blood glucose levels using near-IR transmission through the distal portion of a test subject's index finger. The analytical instrument contains at least one near-infrared energy source for introducing near-infrared energy into the test subject's finger. In one embodiment of the present invention, the introducing means comprises up to six or more near-infrared point sources (near-IR IRED's). IRED's 5 and 6 are shown for illustrative purposes in FIG. 1. The analytical instrument also utilizes detector 8 for detecting near-infrared energy emerging from the test subject's body part. Detector 8 is electrically connected to data processing means 10 which, according to its programming, processes the signal produced by the detector 8 into a signal indicative of the quantity of glucose present in the blood of the test subject. Amplifier 9 amplifies the signal produced by the detector 8 before it is received into the processing means 10.

As illustrated in FIG. 1, the IRED's 5 and 6, detector 8 and processing means 10 are contained within a light-weight hand-held housing unit 1. In a preferred embodiment, housing unit 1 is machined or molded from plastic.

Illustrative IRED's 5 and 6 are separated by light baffle 4 and are positioned so that the near-IR energy is directed through window 14, which may be light scattering, and onto the skin of the test subject. Optical filters, illustrated at 16 and 17, are positioned between each IRED and the window 14 for filtering the near-IR light, thereby optimizing the band of near-IR light striking the subject.

Figure 2:
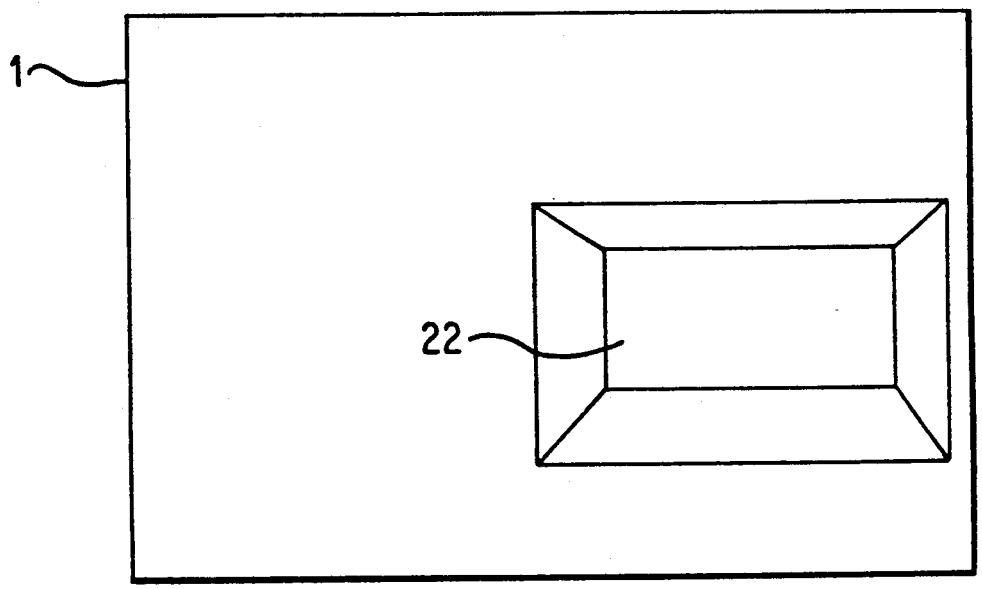
FIG. 2 illustrates a bottom view of the non-invasive glucose measurement instrument of FIG. 1.

An important feature of the present invention is the cartridge means 20 which engages the housing unit. In a preferred embodiment, the cartridge means 20 is replaceable and is plugged into the analysis instrument 1 through receiving port 22 as illustrated in FIG. 2. Cartridge 20 includes electronic memory storage devices 24A and 24B for storing data regarding an individual user and instrument software. By way of example, memory device 24A, such as a RAM, stores a series of glucose readings, the time and the date of all measurements made by the analysis instrument, the total number of measurements made using a particular battery, as well as calibration constants (unique to the individual user) for use by data processor 10. In a preferred embodiment, the memory device 24B is an EPROM-type chip that contains the software for operating the analytical instrument 1, thus facilitating re-programming of instrument 1 by inserting an updated cartridge.

In certain embodiments, cartridge 20 also comprises a power source means, such as the illustrated battery 23, for supplying power to the near-infrared quantitative analysis instrument. Memory devices 24A and 24B and battery 23 are in electrical communication with the processing means 10 via interface 34.

Accurate measurements of the concentration of blood glucose can be made using near-IR quantitative analysis algorithms as discussed in copending U.S. patent application Ser. No. 07/544,580, filed on June 27, 1990. For example, near-IR quantitative analysis algorithms can be used which have only a single variable term, such as the following:

Approximated First Derivative Algorithm
$C = K_0 + K_1 [\log 1/I_G - \log 1/I_H]$ Approximated Second Derivative Algorithm
$C = K_0 + K_1 [\log 1/I_A - 2^*\log 1/I_B + \log 1/I_C]$ Normalized First Derivative Algorithm
$C = K_0 + K_1 \dfrac{[\log 1/I_G - \log 1/I_H]}{[\log 1/I_I - \log 1/I_J]}$ Normalized Second Derivative Algorithm
$C = K_0 + K_1 \dfrac{[\log 1/I_A - 2^*\log 1/I_B + \log 1/I_C]}{[\log 1/I_D - 2^*\log 1/I_E + \log 1/I_F]}$ where C denotes concentration of glucose present in the blood, $K_0$ is the intercept constant, $K_1$ is the line slope of the variable term, and the log 1/I terms each represent an Optical Density (O.D.) value at a particular wavelength.

Figure 4:
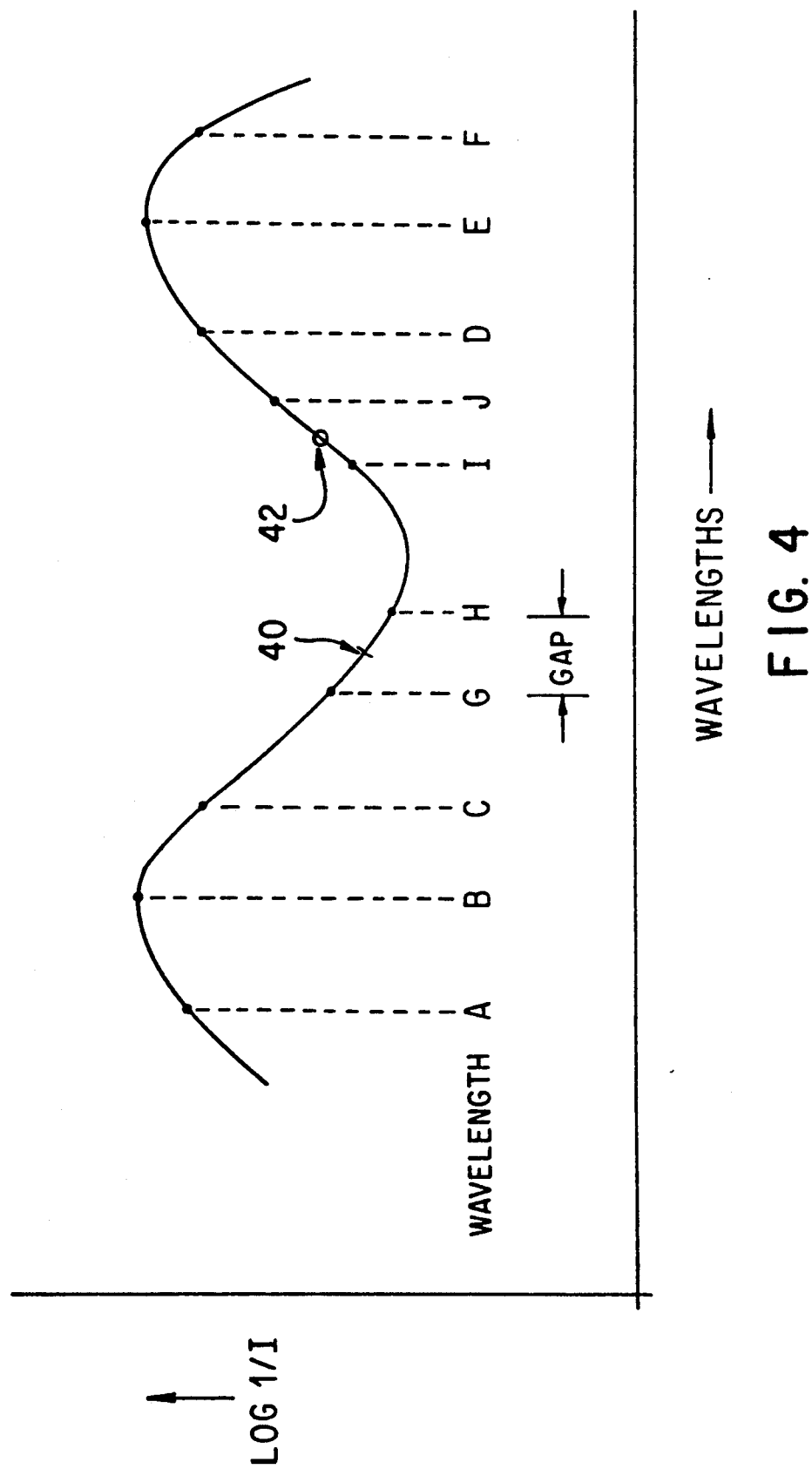
FIG. 4 is a plot of log (1/I) versus wavelength.

In FIG. 4, an example of an overall absorbance curve is shown, wherein log 1/I (O.D.) values for the above algorithms are plotted. In FIG. 4, optical energy is absorbed at wavelength B proportional to the constituent being measured, and optical energy is absorbed at wavelength E proportional to the total substance being measured. Points 40 and 42 are first derivative midpoints. The distance between, for example, wavelength G and wavelength H is referred to herein as the "gap" between two wavelengths. It has been found that a plurality of wavelength pairs, all centered on the same wavelength, can be used in the above algorithms. These algorithms are easily programmed into suitable microprocessor circuitry, such as in processor means 10, by those skilled in the art. The use of these single variable term equations is desirable because it allows simplified instrument calibration, thereby allowing the production of low cost instruments.

The intercept constant $K_0$ and the slope constant $K_1$ are determined by individually calibrating each unit.

Figure 7A:
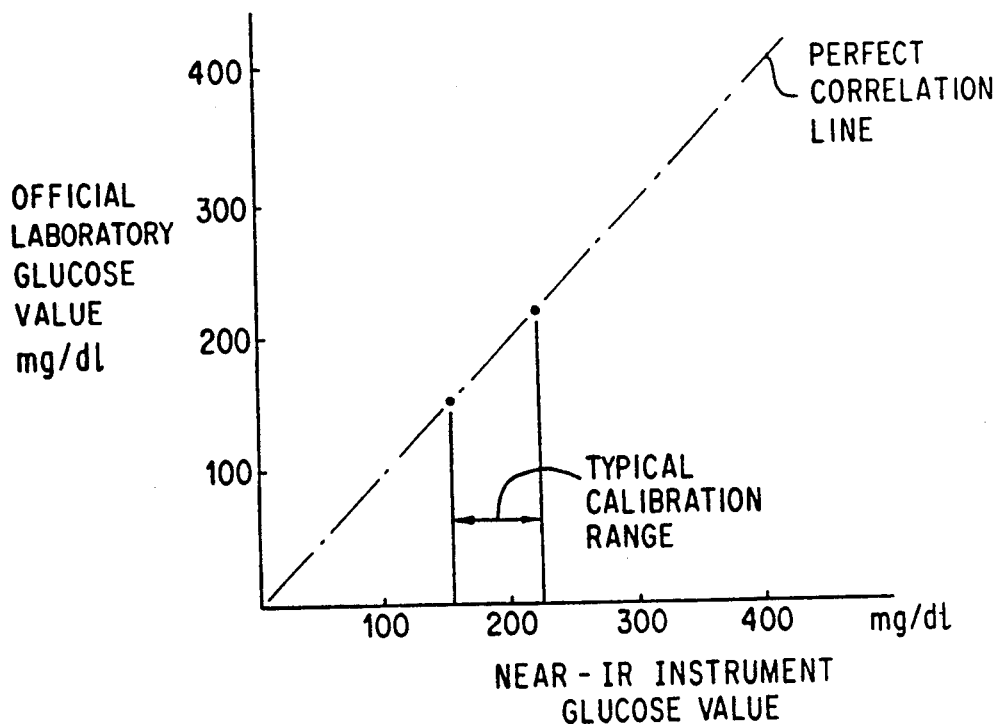
FIGS. 7A-D are plots of official laboratory glucose values versus near-IR instrument glucose values illustrating potential extrapolation errors.
Figure 7B:
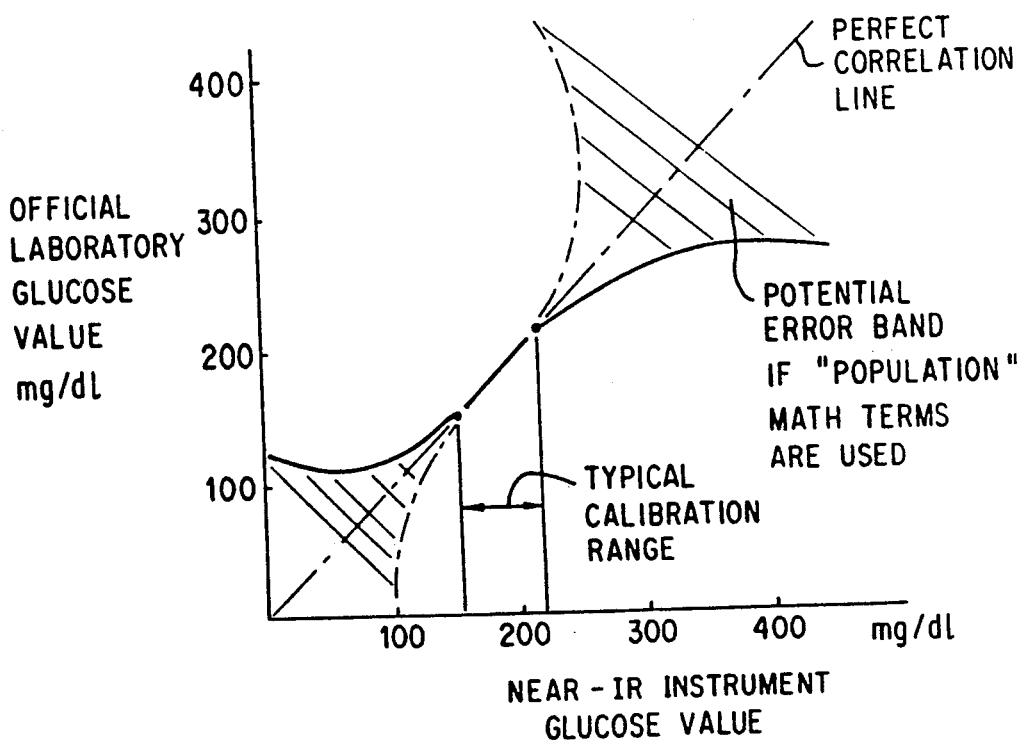

An instrument for non-invasive measurement of blood glucose should provide accurate readings for any individual's glucose level which may be anywhere from about 40 mg/dl to as high as 500 mg/dl. In a typical glucose tolerance test used for calibration, changes in an individual's glucose level can be expected within the range of approximately 50 mg/dl to approximately 150 mg/dl. As a result, providing a custom calibration for an instrument covering the entire range is essentially impossible. Extrapolating information from this small calibration data using the single variable term algorithms shown above can cause errors when measuring glucose levels in the extreme regions of the entire range of possible glucose levels. These potential errors result from the non-linearity of extrapolation values as illustrated in FIGS. 7A and 7B.

Figure 7C:
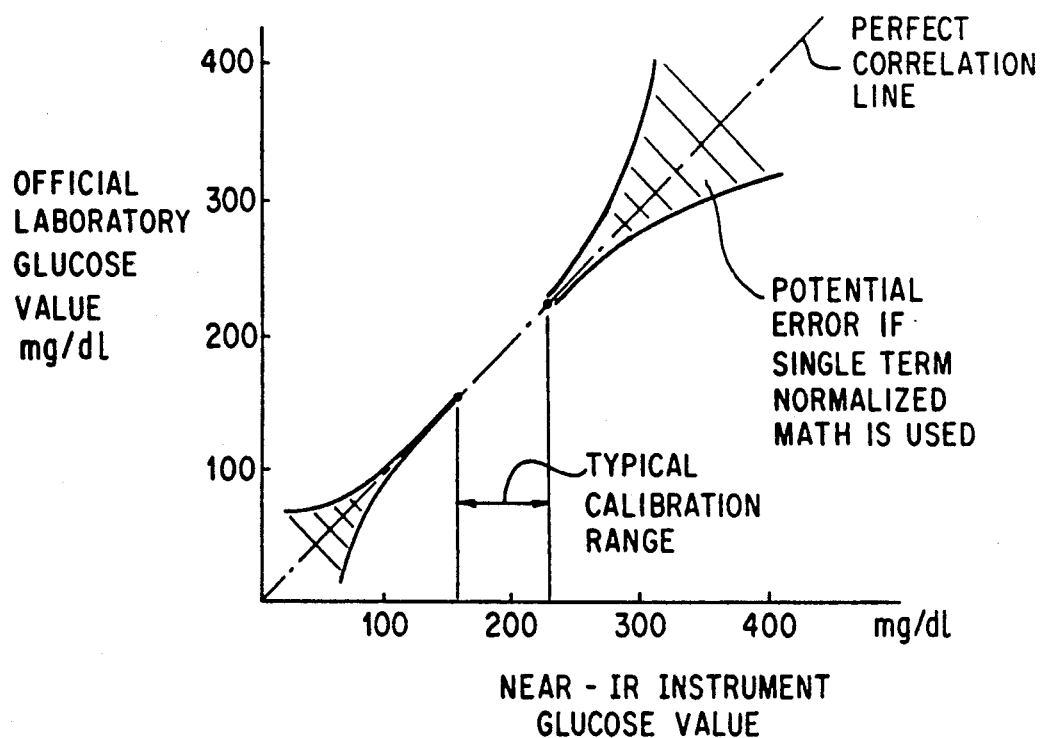
Figure 7D:
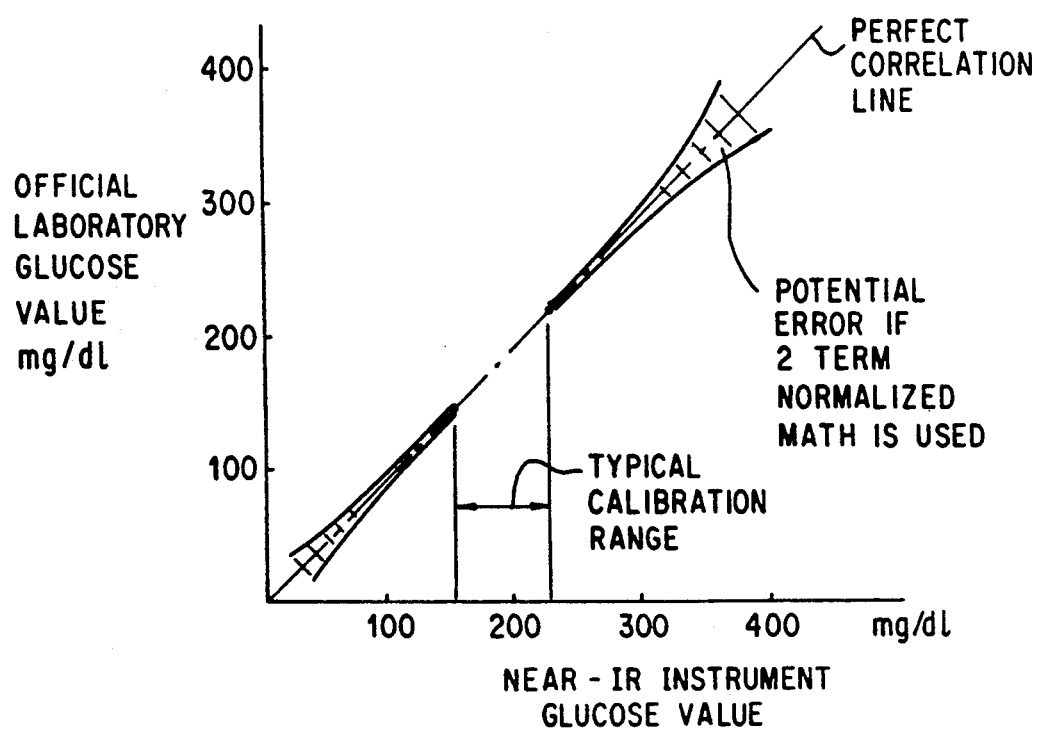

To correct for nonlinear extrapolation, algorithms comprising multiple regression terms are used which enable accurate prediction of blood glucose measurement over a wide range. Such terms can be individual log 1/I terms or can be a multiple number of first or second derivative terms with or without a normalizing denominator. Extrapolation is most reliable, however, using normalized division terms which are self-correcting for many types of measurement variability, as illustrated in FIGS. 7C and 7D. This self-correction occurs because the numerator and denominator normally are multiplied by the same error, thereby self-canceling the error. Examples of these terms include normalized first and second derivative division terms. In one embodiment, algorithms containing two or more of the normalized division terms are used.

Data on a plurality of physical parameters of the test subject can also be utilized in conjunction with multiple wavelength near-infrared analysis, as in prior U.S. Pat. No. 4,633,087, to improve the accuracy of the present blood glucose measurements. Further, blood glucose measurement accuracy can be improved by eliminating error which may result from bias shift in the near-infrared sources as disclosed in copending U.S. Pat. application Ser. No. 07/286,740, incorporated herein by reference.

Selection of combinations of wavelengths which emphasize glucose absorption and remove possible interfering absorptions can be performed by computer search studies, as disclosed in copending U.S. Pat. application No. 07/544,580. In general, a suitable combination of wavelengths will include at least one wavelength which is sensitive to blood glucose, and at least one wavelength which is insensitive to blood glucose (reference wavelength).

In one embodiment of the present invention, the four wavelength model can be used with the following multiple linear regression algorithm:

$$C = K_0 + K_1[log1I_A - log1I_B]/[Log\ 1/I_D - Log\ I_E] + K_2T_S + K_3T_A$$

where $K_0$ through $K_3$ are the calibration constants, A, B, C and D are specific wavelengths where the optical data is being measured, $T_S$ is the local surface temperature of the finger in degrees centigrade divided by 100 and $T_A$ is the temperature of the air within the instrument in degrees centigrade divided by 100. Calibration constants $K_2$ and $K_3$ are independent regression terms which are determined for each individual test subject.

In a preferred embodiment of the present invention, each analytical instrument will be custom calibrated for a specific individual, as disclosed in copending U.S. Pat. application Ser. No. 07/544,580. However, each instrument can be calibrated for a specific individual in any way known to those skilled in the art. For example, calibration can be performed using a continuous glucose monitor whereby a catheter is inserted into a vein. The instrument is calibrated by adjusting its output to correspond to that of the glucose monitor under varying blood glucose concentrations.

Figure 5:
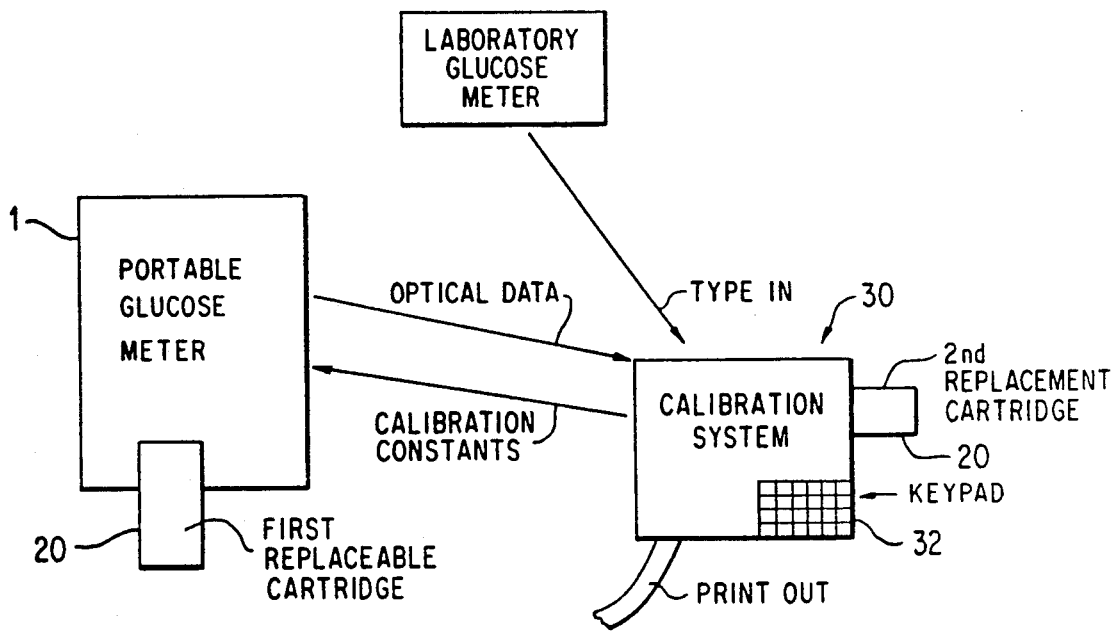
FIG. 5 shows a schematic representation of custom calibration instrumentation according to one aspect of the present invention.

In another aspect of the invention, calibration can be performed using a small number of "finger poke" measurements using either a laboratory instrument (e.g. model 2300G glucose instrument manufactured by Yellow Springs Instrument Co.) or a home-type self test unit. The "finger poke" calibration procedure can be performed in two alternate methods. First, as illustrated in FIG. 5, a calibration system 30 is connected to the analytical instrument 1 and collects both optical data as measurements are taken and the time of each measurement. The calibration system 30 also allows the glucose values from the finger poke measurements to be hand entered via keypad 32 on the calibration system 30 at approximately 15 minute intervals for up to 1.5 hours. When sufficient data has been received, the calibration system performs a multiple regression analysis, calculating the calibration constants for the linear regression algorithms. The calculated calibration constants are then transferred to the replaceable cartridges 20 plugged into the calibration system 30, or into a replaceable cartridge installed in the analytical instrument 1 and another inserted into the calibration system 30. In this approach, the calibration system 30 could be in a doctor's office and could also provide a printout device for the replaceable cartridges.

Figure 6:
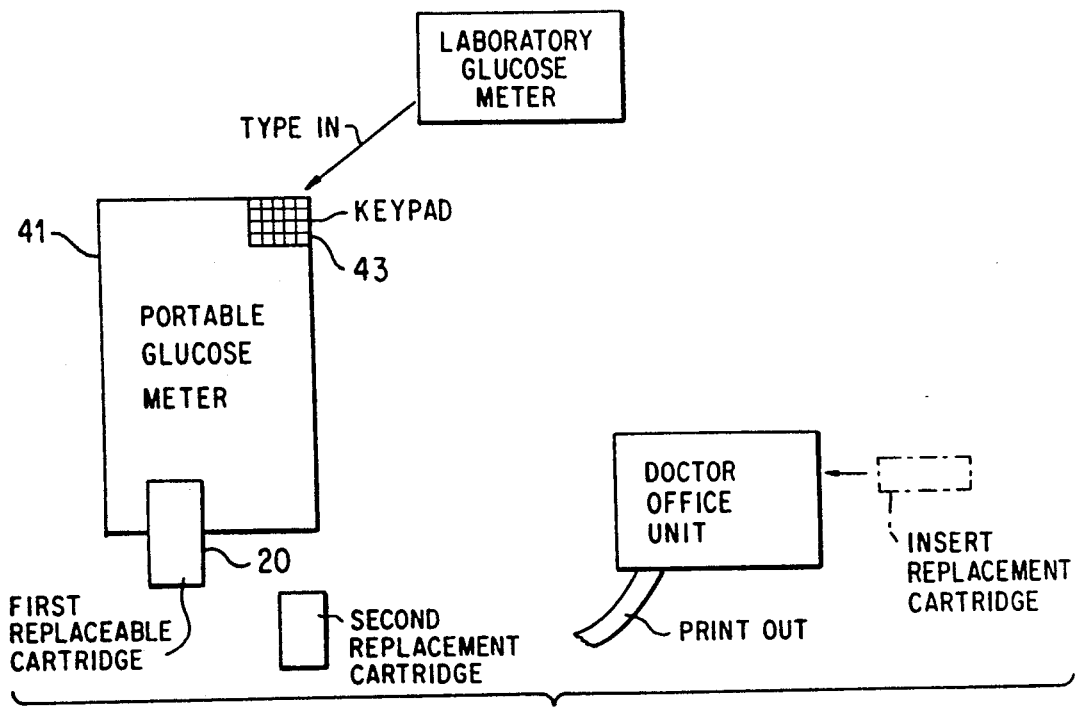
FIG. 6 shows a schematic representation of custom calibration instrumentation according to another aspect of the present invention.

An alternate approach, illustrated in FIG. 6, does not require a calibration system as discussed above. In this approach, the replaceable cartridge contains EPROMs programmed to perform multiple regression analysis. The analytical instrument 41 operates substantially identically as analytical instrument 1 as discussed with reference to FIG. 1 and has a key pad 43 having a minimum of 11 keys (e.g. "0" through "9" plus an ENTER key) to allow the finger poke readings to be entered. In another embodiment, the finger poke readings are entered from an external keyboard or a replaceable cartridge. After the regression analysis is performed, the analytical instrument stores the calibration constants in the replaceable cartridge. At the same time, the analytical instrument erases the regression program allowing the EPROM to be used to store time/data and glucose values for a predetermined period of time, e.g., three months. The instrument shown in FIG. 6 also allows the analytical instrument 41 to temporarily store calibration constants in a RAM, thus allowing a second replaceable cartridge to be inserted therein, after the first replaceable cartridge is removed. In addition, a low cost printer allow the data stored within the replaceable cartridges to be printed.

Each replaceable cartridge 20 is identified as belonging to a specific individual, because it contains custom calibration values for that individual. A user protection means is provided to insure that a replacement cartridge containing an individual's calibration information is used only by that individual, in the proper unit. In one embodiment, user protection is accomplished by a "handshake" code transmitted between the replacement cartridge and the unit. The encoding procedure comprises copying one or more calibration constants in the cartridge into the unit, which constant is used as the "handshake." In a preferred embodiment, all calibration constants for a particular individual are used as the "handshake."

In the embodiment shown in FIG. 1, wavelengths for conducting the near-IR analysis are chosen so as to yield accurate glucose measurement levels. In one embodiment, the wavelengths are approximately $A=771$ nm, $B=791$ nm, $C=1070$ nm and $D=1080$ nm. The 771 nm and 791 wavelengths can be obtained using standard 880 nm center wavelength IREDs in combination with narrow bandpass filters. IREDs having center wavelengths at longer wavelengths, such as the standard 950 nm IRED, are useful for producing 1070 nm and 1080 nm output when combined with appropriate optical filters. In a preferred embodiment, the wavelengths are approximately $A=667$ nm, $B=687$ nm, $D=1059$ nm and $E=1079$ nm.

It is very important that the test subject's fingertip not be exposed to ambient light. Further, it is desireable that the actual measurement be made near the rear of the finger nail. Finger stop 30 illustrated in FIG. 1 facilitates properly positioning the test subject's finger. FIG. 1 also illustrates a finger retainer 2 to securely position the user's finger inside the instrument and to provide sufficient blockage of ambient light. Spring 21 pushes the finger retainer 2 against the bottom of the test subject's finger thereby providing a secure fit. Linear potentiometer 19 is connected to finger retainer 2 and can measure an individual's finger thickness. In addition, an inflatable diaphragm or rubber/foam iris (illustrated at 15) is used to secure the test subject's finger and shield light. The inflatable diaphragm can measure the blood pulse as well.

In a preferred embodiment, light shielding cover 7, shown in FIG. 1, is rotatably attached to the analytical instrument 1 and closes over the finger chamber 28 providing essentially total blockage of ambient light. Cover 7 extends along the entire side of the analytical instrument and is securable at the base thereof in recess 33. Rubber strip 13 is secured to cover 7 and further facilitates blocking ambient light.

To facilitate the instrument's use by both adults and children, the finger measurement sections of the instrument allow for two or more different sizes of inserts. As illustrated in FIGS. 8A and 8B insert 31A is suitable for the size of adult fingers and insert 31B is suitable for the size of children's fingers. Inserts accommodating a finger of any size can be used.

FIG. 1 further illustrates an LCD display 18. Display 18 is advantageously constructed in a large size to facilitate reading by potential users who may have poor eyesight, one of the side effects of diabetes.

In a preferred embodiment, the analytical instrument comprises means for displaying blood glucose level in two systems: the mg/dl unit for U.S. use and the mmol/L unit for Canadian use. Processor means 10 shown in FIG. 1 can perform this function. A change between the two display modes would typically be made during initial setup. Thus, a slide type switch (not shown) positioned in a non-convenient place (e.g., in the battery compartment) could be used to select the desired display.

Figure 3:
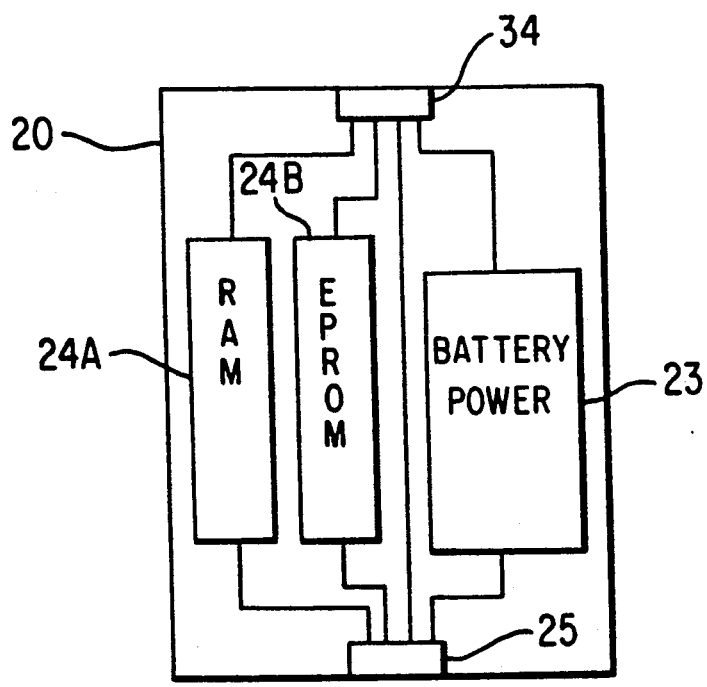
FIG. 3 shows a schematic representation of a replaceable cartridge according to the present invention.

FIG. 3 shows input/output connector 25 which forms part of the replaceable cartridge 20 and is electrically connected to controller/processor 10 of the analytical instrument 1. Input/output connector 25 allows the analytical instrument 1 to be connected to a "host instrument" which enables calibration constants determined by the host instrument, as described above, to be automatically transferred to the analytical instrument during calibration setup. In addition, the input/output connector 25 can be attached to an external keypad which allows manual entry of calibration constants.

The operation of the near-infrared quantitative analysis instrument will be readily apparent. Prior to making a finger measurement, a front panel push button 26 is pressed which provides for optical standardization. Optical standardization is accomplished by measuring the empty finger chamber. Standardization also can include a "dark correction" measurement with all IREDs off so that a light leak is detected and automatically corrected for.

FIG. 1 illustrates that when the finger is inserted into chamber 28, a built-in thermistor 29 measures the finger's temperature. The temperature measurement will be made at two times, approximately five seconds apart, with a temperature reading being determined by using a logarithmic prediction equation as described in U.S. Pat. No. 4,286,376. Care should be taken to ensure that the finger holder 2 fits securely enough around the finger so as to block out light, and yet loosely enough to ensure that pulse beating does not interfere with the measurement. Better precision can be achieved if a single measurement involves inserting the finger twice.

A second thermistor 27 is positioned inside the analytical instrument 1 for measuring the ambient air temperature therein. The ambient air temperature measurement could be made at any time prior to the instrument's actual use, but preferably at the time the optical standard is measured. No logarithmic prediction is needed for the instrument air temperature measurement. Also, timing control means 11 in processor means 10 provides a battery protection feature which shuts off the instrument within a predetermined period of time after the a measurement is taken. In a preferred embodiment of the present invention, the battery protection feature shuts off the instrument within approximately two minutes of the last measurement. Although one may additionally be provided, this protection feature would alleviate the need for an "Off" button.

Processor means 10 and memory devices 24A and 24B advantageously enable a user to recall his or her previous glucose readings, including the time and date of those readings. In a preferred embodiment, between approximately eight and ten prior readings can be recalled in reverse order.

The analytical instrument preferably comprises means for indicating on display 18 the number of days remaining before the replaceable cartridge must be changed. This information can be accessed from memory device 24A at any time by pressing push button 26. In a preferred embodiment, this information will automatically appear on display 18 when the instrument is turned on, beginning five days prior to replacement. The analytical instrument 1 also includes a battery protection feature which prevents excessive battery use. During the calibration process, many battery-draining optical scans are required. In a preferred embodiment, pre-programmed circuitry permits a user to make no more than five successive readings without waiting a minimum of ten minutes before taking further readings.

In other versions, the analytical instrument utilizes a speech synthesizer 12 electrically connected to processor means 10 for providing instrument speech capability. This feature is used to provide patient prompting as well as providing an audio readout. This is of particular value to patients whose eyesight is excessively poor.

In another aspect of the present invention, a lightweight hand-held instrument uses the principle of light interactance to measure blood glucose level non-invasively by locating an optical transmitter and a detector on the skin surface near either an artery or vein. An instrument of this general description is disclosed in co-pending application Ser. No. 07/298,904.

In a lightweight, hand-held interactance analysis instrument 50 illustrated in FIG. 9, included is one or more means for providing at least one point source of near-infrared energy of a predetermined bandwidth of interest which is positioned within a first chamber 60 of the instrument 50. The near-infrared point source means is positioned so that near-infrared energy being emitted from the point source means will be focussed by lens 52 through window 54 and onto the skin of the test subject. The near-infrared point source means may comprise one or a plurality of infrared emitting diodes (IREDs). Two such IREDs 56 and 58 are illustrated in FIG. 9. In other embodiments employing a plurality of IREDs, three, four or more IREDs may be utilized as the point source means.

An optical detector, illustrated schematically in FIG. 9 and designated by reference numeral 68, is disposed within a lower end portion of second chamber 70. Inner wall 74 is positioned between detector 68 and illumination section 60, thereby providing an optically-isolated mask which prevents near infrared radiation from the point source means and/or lens 52 from impinging directly on detector 68. A near-infrared optical detector 68 generates an electrical signal when near-infrared radiation is detected thereby.

The optical detector 68 is connected to the input of an electrical signal amplifier 62 by suitable electrical conducting means 63. Amplifier 62 may be an inexpensive integrated circuit (IC) signal amplifier, and amplifies the signals generated when near-IR energy strikes detector 68. The output of amplifier 62 is fed to a controller/data processor and display driver 64 which provides a signal to readout device 66.

Figure 10:
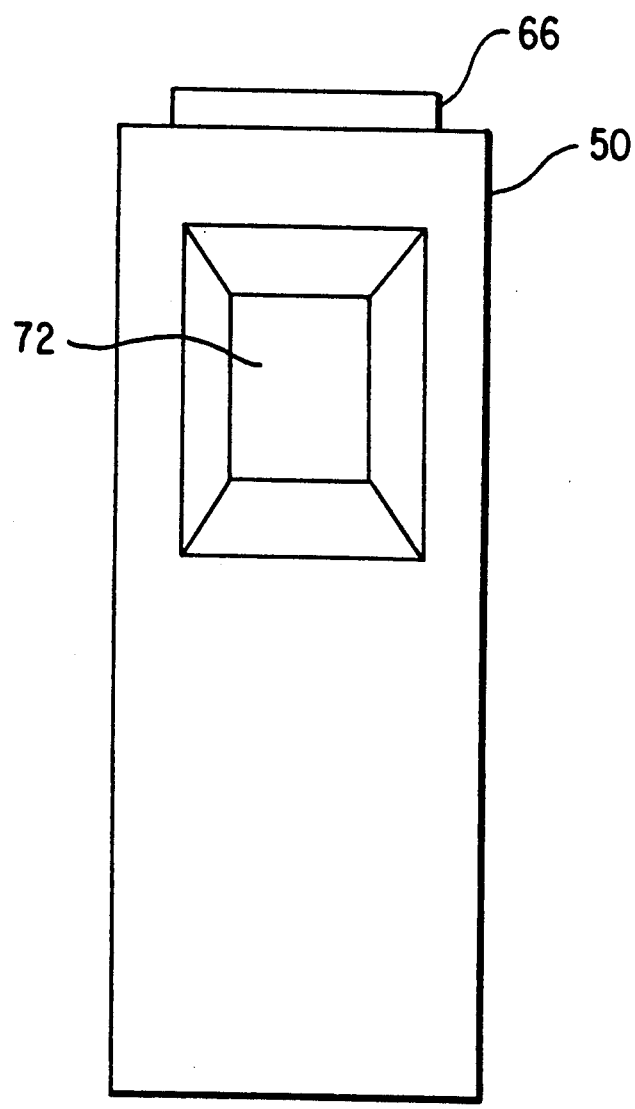
FIG. 10 shows a side view of the interactance instrument of FIG. 9.

Interactance analysis instrument 50 further includes a replaceable cartridge means 80 which engages the housing unit. In a preferred embodiment, the cartridge means 80 is plugged into the analysis instrument 50 through receiving port 72 as illustrated in FIG. 10. Cartridge 80 is substantially identical to cartridge 20 discussed above and includes a battery power source 76, an electronic memory storage device 78A, such as a RAM, for storing date regarding an individual user and memory storage device 78B, such as an EPROM, for storing the instrument's software. In addition, cartridge 80 performs the same operational functions as disclosed with reference to cartridge 20. Memory devices 78A and 78B and battery 76 are in electrical communication with controller/data processor 64 via interface 79.

In use, the analysis instrument 50 is positioned so that its flat bottom surface rests on the skin directly above a prominent vein of the wrist of the test subject. Interactance instrument 50 is particularly useful for measuring the blood glucose level of small children whose fingers may be too small to achieve accurate results using the analysis instrument of FIG. 1.

Although the invention has been described in connection with certain preferred embodiments, it is not limited to them. Modifications within the scope of the following claims will be apparent to those skilled in the art. For example, accurate measurements can be obtained from body parts other than the wrist and the finger. The algorithm used to calculate blood constituent concentration(s) can be altered in accordance with known near-infrared analytical techniques.

I claim:

1. A near-infrared quantitative analysis instrument for non-invasive measurement of blood present in a body part of a subject, comprising:
   (a) introducing means including a near infrared energy source for introducing near-infrared energy into blood present in a body part of a subject;
   (b) detecting means for detecting near-infrared energy emerging from the body part;
   (c) positioning means for positioning both the near-infrared introducing means and the detecting means closely adjacent to the body part;
   (d) processing means for processing a first electrical signal produced by the detector means into a second signal indicative of the quantity of glucose present in the blood of the subject;
   (e) a housing means for housing said introducing means, said detecting means and said processing means; and
   (f) a replaceable cartridge means engaging said housing means comprising a memory means for storing data comprising said second signal.

2. A near-infrared quantitative analysis instrument of claim 1 wherein said near-infrared energy source comprises an infrared emitting diode.

3. An analysis instrument of claim 1 wherein said introducing means comprises a filter means for selectively transmitting near-infrared energy, said filter means being disposed between said source and said body part.

4. An analysis instrument of claim 3 comprising a first filter means for selectively transmitting near-infrared energy of between about 780 and 810 nanometers and a second filter means for selectively transmitting near infrared energy of between about 1070 and 1090 nanometers.

5. An analysis instrument of claim 1 wherein said memory means for storing data is electrically connected to said processing means which comprises a clock means for storing times at which measurement data is stored in said memory means.

6. An analysis instrument of claim 5 wherein said memory means further comprises programmable means for storing software for operating the analytical instrument.

7. An analysis instrument of claim 6 wherein said programmable means comprises an erasable programmable read only memory.

8. An analysis instrument of claim 1 wherein said cartridge means further comprises a power source means for providing power to said analysis instrument.

9. An analysis instrument of claim 1 further comprising an input/output connection means for enabling data to be input to said processing means and for outputting to an external source data from said processing means.

10. An analysis instrument of claim 9 wherein said cartridge means comprises said input/output connection means.

11. An analysis instrument of claim 1 wherein said housing means comprises a retainer means for securely positioning said body part in said housing means.

12. An analysis instrument of claim 1 wherein said housing means further comprises means for shielding the detector means from exposure to ambient light.

13. An analysis instrument of claim 12 wherein said means for shielding the detector means comprises a cover rotatably secured to said housing means.

14. An analysis instrument of claim 1 further comprising a display means for displaying blood glucose level.

15. An analysis instrument of claim 14 wherein said display means displays blood glucose levels in mg/dl and mmol/L units.

16. An analysis instrument of claim 1 wherein said housing means further comprises a first temperature sensing means electrically connected to said processor means for sensing a skin temperature of said body part and producing a first temperature signal representative thereof.

17. An analysis instrument of claim 1 wherein said housing means further comprises a second temperature sensing means electrically connected to said processor means for sensing ambient temperature inside said instrument and producing a second temperature signal representative thereof.

18. An analysis instrument of claim 1 wherein the processing means processes the first signal according to the formula $$C = K_0 + K_1[\log 1/I_A - \log 1/I_B] + K_2 T_S$$

wherein C is concentration of glucose present in the blood, $K_0$ is an intercept constant, $K_1$ is the line slope of $$[\log 1/I_A - \log 1/I_B]$$

$K_2$ is a calibration constant, log $1/I_A$ and log $1/I_B$ each represent an optical density value at corresponding wavelengths A and B and $T_S$ represents the local surface temperature of said body part.

19. An analysis instrument of claim 1 wherein the signal processing means processes the first signal according to the formula $$C = K_0 + K_1[\log 1/I_A - 2^*\log 1/I_B + \log 1/I_C] + K_2 T_1$$

wherein C is concentration of glucose present in the blood, $K_0$ is an intercept constant, $K_1$ is line slope of $$[\log 1/I_A - 2^*\log 1 I_B + 1/I_C]$$

$K_2$ is a calibration constant, log $1/I_A$, log $1/I_B$, and log $1/I_C$ each represent an optical density value at corresponding wavelengths A, B and C, and Ts represents the local surface temperature of said body part.

20. An analysis instrument of claim 1 wherein the signal processing means processes the signal according to the formula $$C = K_0 + K_1 \frac{[\log 1/I_A - \log 1/I_B]}{[\log 1/I_D - \log 1/I_E]} + K_2 T_S$$

wherein C is concentration of glucose present in the blood, $K_0$ is an intercept constant, $K_1$ is the line slope of $$\frac{[\log 1/I_A - \log 1/I_B]}{[\log 1/I_D - \log 1/I_E]}$$

$K_2$ is a calibration constant, log $1/I_A$, log $1/I_B$, log $1/I_D$ and log $1/I_E$ each represent an optical density value at corresponding wavelengths A, B, D and E and $T_S$ represents the local surface temperature of said body part.

21. An analysis instrument of claim 1 wherein the signal processing means processes the signal according to the formula $$C = K_0 + K_1 \frac{[\log 1/I_A - 2^*\log 1/I_B + \log 1/I_C]}{[\log 1/I_D - 2^*\log 1/I_E + \log 1/I_F]} + K_2 T_S$$

wherein C is concentration of glucose present in the blood, $K_0$ is an intercept constant, $K_1$ is the line slope of $$\frac{[\log 1/I_A - 2^*\log 1/I_B + \log 1/I_C]}{[\log 1/I_D - 2^*\log 1/I_E + \log 1/I_F]}$$

$K_2$ is a calibration constant, log $1/I_A$, log $1/I_B$, log $1/I_C$, log $1/I_D$, log $1/I_E$, and log $1/I_F$ each represent an optical density value at corresponding wavelengths A, B, C, D, E and F, and $T_S$ represents the local surface the temperature of said body part.

22. An analysis instrument of claim 1 wherein the first signal processing means processes the signal according to the formula $$C = K_0 + K_1 \frac{[\log 1/I_A - \log 1/I_B]}{[\log 1/I_D - \log 1/I_E]} K_2 T_S + K_3 T_A$$

wherein C is concentration of glucose present in the blood, $K_0$ is an intercept constant, $K_1$ is the line slope of $$\frac{[\log 1/I_A - \log 1/I_B]}{[\log 1/I_D - \log 1/I_E]}$$

$K_2$ and $K_3$ are calibration constants, log $1/I_A$, log $1/I_B$, and log $1/I_D$ and log $1/I_E$ each represent an optical density value at corresponding wavelengths A, B, D and E, $T_S$ represents the local surface temperature of said body part and $T_A$ represents the ambient air temperature of said instrument.

23. An analysis instrument of claim 1 wherein the first signal processing means processes the signal according to the formula $$C = K_0 + K_1 \frac{[\log 1/I_A - 2^*\log 1/I_B + \log 1/I_C]}{[\log 1/I_D - 2^*\log 1/I_E + \log 1/I_F]} K_2 T_S + K_3 T_A$$

wherein C is concentration of glucose present in the blood, $K_0$ is an intercept constant, $K_1$ is the line slope of $$\frac{[\log 1/I_A - 2 \cdot \log 1/I_B + \log 1/I_C]}{[\log 1/I_D - 2 \cdot \log 1/I_E + \log 1/I_F]}$$

$K_2$ and $K_3$ are calibration constants, $\log 1/I_A$, $\log 1/I_B$, $\log 1/I_C$, $\log 1/I_D$, $\log 1/I_E$, and $\log 1/I_F$ each represent an optical density value at corresponding wavelengths A, B, C, D, E and F, $T_r$ represents the local surface the temperature of said body part and $T_A$ represents the ambient temperature of said instrument.

24. An analytical instrument of claim 1 further comprising protection means for requiring that said cartridge which is custom calibrated for an individual be used in a specific analytical instrument.

25. An analytical instrument of claim 24 wherein said protection means comprises storing at least one calibration constant in each said specific analytical instrument and said cartridge which must be matched before the analytical instrument will operate.

26. An analytical instrument of claim 1 further comprising speech synthesizer means for providing audio operational instructions and audio output corresponding to said second signal.

27. An analytical instrument of claim 1 wherein said processor means further comprises means for automatically correcting for bias drift in said second signal.

* * * * *